(12) United States Patent　(10) Patent No.: US 6,520,947 B1
Tilly et al.　(45) Date of Patent: Feb. 18, 2003

(54) DISPOSABLE ABSORBENT ARTICLE HAVING REUSABLE FASTENING MEANS

(75) Inventors: Edgar Lionel Tilly, Eschborn (DE); Eric-Joachim Willms, Altdorf (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/806,885

(22) PCT Filed: Oct. 6, 1999

(86) PCT No.: PCT/US99/23298

§ 371 (c)(1),
(2), (4) Date: Apr. 5, 2001

(87) PCT Pub. No.: WO00/23025

PCT Pub. Date: Apr. 27, 2000

(30) Foreign Application Priority Data

Oct. 16, 1998 (EP) ............................................. 98119574

(51) Int. Cl.[7] .................................................. A61F 13/15
(52) U.S. Cl. .................... 604/391; 604/392; 604/358; 428/99; 428/172; 428/157
(58) Field of Search ................................. 604/397, 389, 604/391; 428/172, 157, 99

(56) References Cited

U.S. PATENT DOCUMENTS

| 3,860,003 A | 1/1975 | Buell |
| 4,315,508 A | 2/1982 | Bolick |
| 5,669,901 A | 9/1997 | LaFortune et al. |
| 5,776,123 A | * 7/1998 | Goerg et al. ................ 604/391 |

FOREIGN PATENT DOCUMENTS

| EP | 0 605 012 A1 | 7/1994 |
| EP | 0 605 013 A1 | 7/1994 |
| WO | WO 85/03205 A1 | 8/1985 |

OTHER PUBLICATIONS

PCT International Search Report for PCT/US99/23298, date of mailing: Jan. 19, 2000.

* cited by examiner

*Primary Examiner*—John J. Calvert
*Assistant Examiner*—Angela Grayson
(74) *Attorney, Agent, or Firm*—Michael S. Kolodesh; Jeffery R. Moore; Jay A. Krebs

(57) ABSTRACT

The present invention relates to disposable absorbent articles such as diapers, adult incontinence products, sanitary napkins and the like comprising a reusable fastening device. The reusable fastening device comprises a first end a second end member, and a suspension member. Both end members are releasably engageable with the suspension member and releasably engageable with the disposable absorbent article.

5 Claims, 2 Drawing Sheets

DISPOSABLE ABSORBENT ARTICLE HAVING REUSABLE FASTENING MEANS

FIELD OF THE INVENTION

The present invention relates to articles which absorb and/or contain bodily exudates, including disposable absorbent articles such as diapers, adult incontinence products, sanitary napkins and the like. More particularly, the invention relates to disposable absorbent articles comprising a reusable fastening device.

BACKGROUND OF THE INVENTION

The major function of disposable absorbent articles such as diapers and adult incontinence briefs is to prevent body exudates from soiling, wetting, or otherwise contaminating clothing or other articles, such as bedding, that come in contact with the wearer. In recent years, disposable diapers, such as those disclosed in U.S. Pat. No. 3,860,003 issued to Kenneth Barclay Buell on Jan. 14, 1975, have become very popular with the public and have generally replaced durable cloth absorbent articles because of their convenience and reliability.

Such disposable absorbent articles are worn about the lower torso of the wearer to be registered with the urethra and the anus of the wearer during use. Usually, the absorbent article being of generally rectangular shape (some have notches cut out along the sides to accommodate the legs of the wearer) is affixed around the lower torso of the wearer by a fastening system that joins the front waist end of the absorbent article to the rear waist end of the absorbent article. Such fastening systems generally comprise a first end member joined to the front waist end of the absorbent article and a second end member joined to the rear waist end of the absorbent article, and a suspension member connecting the first end member with the second end member.

Typically, such fastening systems are permanently attached to the back waist region of the absorbent article and are releasably attachable to the front waist region of the absorbent article. The releasable attachment can be achieved by hooks, buttons, press studs, adhesive tapes, mechanical fastening such as hook and loop type mechanical fastening, or the like.

However, despite the effectiveness of such fastening systems, due to their permanent attachment to the absorbent article they have to be disposed of together with the article once the absorbent article is either saturated or soiled with body exudates such as urine and feces.

Disposable absorbent articles of the prior art such those disclosed in U.S. Pat. No. 4,315,508 issued to Bolick and in U.S. Pat. No. 5,669,901 issued to LaFortune, have addressed this problem by comprising a fastening systems that is releasably attachable to the front waist end and to the back waist end.

However, these fastening system still have to be disposed of entirely even if only a small part of it such as one end member has been soiled.

Accordingly, it would be desirable to provide an disposable absorbent article comprising a reusable fastening system that can be separated into its individual components. Thus, only those components which have been soiled have to be disposed of, all other components may be reused.

SUMMARY OF THE INVENTION

The present invention is a disposable absorbent article having a first waist region and a second waist region, comprising a topsheet, a backsheet at least partially peripherally joined to said topsheet, an absorbent means positioned intermediate said topsheet and said backsheet, and a reusable fastening device. The reusable fastening device comprises a first end member, a second end member, and a suspension member. The first end member of the reusable fastening device is releasably engageable the first waist region and releasably engageable with the suspension member. The second end member of the reusable fastening device is releasably engageable with the second waist region and releasably engageable with the suspension member.

BRIEF DESCRIPTION OF THE DRAWINGS

While the specification concludes with claims particularly pointing out and distinctly claiming the subject matter which is regarded as the present invention, it is believed that the description will be better understood from the following descriptions which are taken in conjunction with the accompanying drawings in which like designations are used to designate substantially identical elements.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). As used herein, the term "unitary" is used to mean that one or more element(s) of the article is or are formed (joined and positioned) in a particular place or position as a unitary structure with other elements of the article or as a separate element joined to another element of the article. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element. A "unitary" absorbent article refers to absorbent articles which are formed of separate parts united together to form a coordinated entity so that they do not require separate manipulative parts like a separate holder and liner. A particular embodiment of an absorbent article of the present invention is the unitary disposable absorbent article, diaper 20, shown in FIG. 1. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, and the like.

Figure 1:
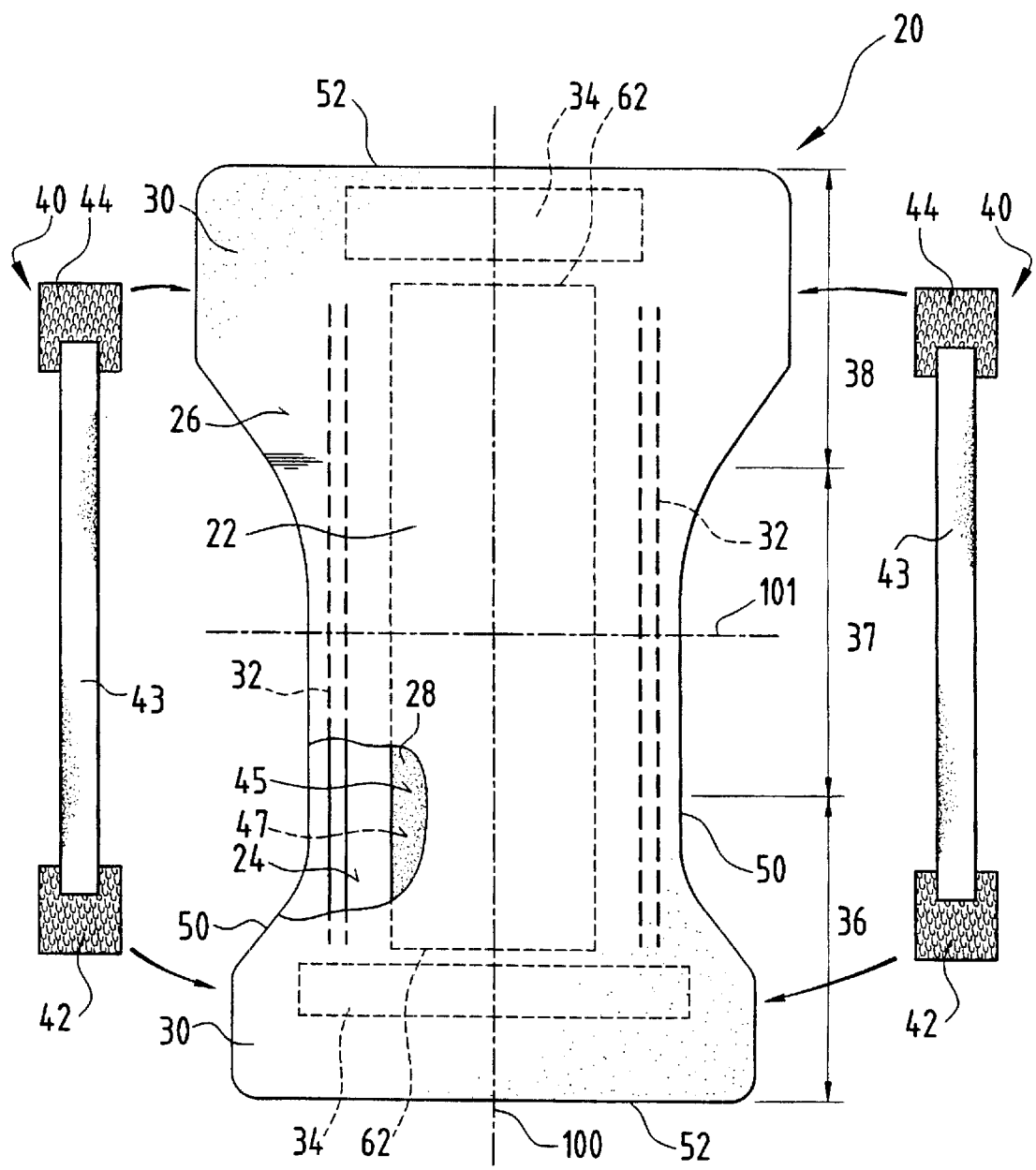
FIG. 1 shows a plane view of one embodiment of the disposable absorbent article of the present invention.

FIG. 1 is a plan view of the diaper 20 of the present invention in a flat-out, state with portions of the structure being cut-away to more clearly show the construction of the diaper 20. The portion of the diaper 20 which faces the garment during use is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening device generally designated 40. The fastening device comprises a first end member 42, a suspension member 43, and a second end member 44. Diaper 20 is shown in FIG. 1 to have a first Waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 101 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use. For unitary absorbent articles, the chassis 22 comprises the main structure of the diaper with other features added to form the composite diaper structure. While the topsheet 24, the backsheet 26, and the chassis 22 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993. Other suitable diaper chassis design are disclosed in U.S. Pat. No. 5,569,232 entitled "Absorbent Article With Multiple Zone Structural Elastic-Like Film Web Extensible Waist Feature" which issued to Roe et al. on Oct. 29, 1996; U.S. Pat. No. 5,554,144 entitled "Absorbent Article With Multiple Zone Structural Elastic-Like Film Web Extensible Waist Feature" which issued to Roe et al. on Sep. 10, 1996; U.S. Pat. No. 5,554,143 entitled "Absorbent Article With Multiple Zone Structural Elastic-Like Film Web Extensible Waist Feature" which issued to Roe et al. on Sep. 10, 1996; U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,556,394 entitled "Absorbent Article With Multiple Zone Structural Elastic-Like Film Web Extensible Waist Feature" which issued to Roe et al. on Sep. 17, 1996. Each of these references is hereby incorporated by reference herein.

The disposable absorbent article of the present invention is worn around the lower torso by putting the article between the legs of the wearer and subsequently connecting the first waist region with the second waist region by means of the fastening devices. Thereby, the fastening devices may be put around the waist of the wearer such that first waist region the second waist region in association with two fastening devices completely circumscribe the waist of the wearer. Another possibility to hold the diaper around the lower torso of the wearer, is by using the fastening devices of the present invention in a suspender fashion, i.e. by putting the fastening devices over the shoulders of the wearer.

The suspension member of the fastening device of the present invention has a longitudinal dimension, a transverse dimension, and a thickness dimension substantially smaller than the longitudinal dimension and the transverse dimension. Preferably, the transverse dimension is substantially smaller than the longitudinal dimension. The longitudinal dimension of the suspension member is between 1 centimeter and 200 centimeters, depending on the size of the wearer and on the intended way to fix the diaper around the lower torso of the wearer. The transverse dimension of the suspension device is between 1 and 20 centimeters, preferably between 2 and 15 centimeters, more preferably between 3 and 10 centimeters, most preferably 5 centimeters.

The first and second end members of the fastening device of the present invention have a longitudinal dimension, a transverse dimension, and a thickness dimension substantially smaller than the longitudinal dimension and the transverse dimension. Preferably, the transverse dimension is substantially smaller than the longitudinal dimension. The longitudinal dimension of the first and second end members is between 1 centimeter and 20 centimeters, preferably between 2 and 15 centimeters, more preferably between 3 and 12 centimeters, most preferably about 10 centimeters. The transverse dimension of the first and second end members is between 0.5 cm and 10 cm, preferably between 1 cm and 5 cm, and more preferably between 1 cm and 3 cm.

The fastening devices of the present invention, i.e. the suspension members and the end members, may be made from web materials. The term "web material" as used herein refers to a sheet-like material, or to a composite or laminate comprising two or more sheet-like materials. For example, a web material can be a fibrous web, a non-fibrous web, a foam, or the like.

A suitable web material is a fibrous web, such as a tissue web, a non-woven web, a woven web, a knit web, or the like. Such fibrous webs can comprise natural fibers (e.g., wood or cotton fibers), synthetic fibers (e.g., polyester or polypropylene fibers), or a combination of natural and synthetic fibers. The non-woven web materials may be made—without limiting to these—by processes commonly referred to as spunlace, spunbond, meltblown, carded, and/or air-through or calendar bonded. The fibrous webs of the present invention may be absorbent or non-absorbent, liquid pervious, or liquid impervious.

Another suitable web material is a non-fibrous web such as a film. Non-fibrous web materials of the present invention may be comprised of polyolefins such as polyethylenes, including linear low density polyethylene (LLDPE), low density polyethylene (LDPE), ultra low density polyethylene (ULDPE), high density polyethylene (HDPE), or polypropylene and blends thereof with the above and other materials. Examples of other suitable polymeric materials which may also be used include, but are not limited to, polyester, polyurethanes, compostable or biodegradable polymers, heat shrink polymers, thermoplastic elastomers, metallocene catalyst-based polymers (e.g., INSITE™. available from Dow Chemical Company and Exxact™ available from Exxon), and breathable polymers.

The non-fibrous web material may also be comprised of an apertured film, macroscopically expanded three-dimensional formed film, absorbent or foam, filled composition, or laminates and/or combinations thereof.

Suitable web materials for the present invention include laminates of the above mentioned materials. Laminates may be combined by any number of bonding methods known to those skilled in the art. Such bonding methods include but are not limited to thermal bonding, adhesive bonding (using any of the number of adhesives including but not limited to spray adhesives, hot melt adhesives, latex based adhesives and the like), sonic bonding and extrusion laminating whereby a polymeric film is cast directly onto a substrate, and while still in a partially molten state, bonds to one side of the substrate, or by depositing meltblown fibers nonwoven directly onto a substrate.

In one embodiment of the fastening device of the present invention, the second releasably engageable member substantially extends over the entire surface of the suspension member. In another embodiment, the second releasably engageable member extends over one of the two major surfaces of the suspension member. The second releasably engageable member may also be unitary with the suspension member. In another embodiment of the fastening device of the present invention, two second releasably engageable members are positioned adjacent to the two longitudinal ends of the suspension member.

The releasable engagement between the end members and the suspension member of a fastening device of the present invention can be achieved by hooks, buttons, press studs, adhesive tapes, mechanical fastening such as hook and loop type mechanical fastening, or the like.

Figure 2:
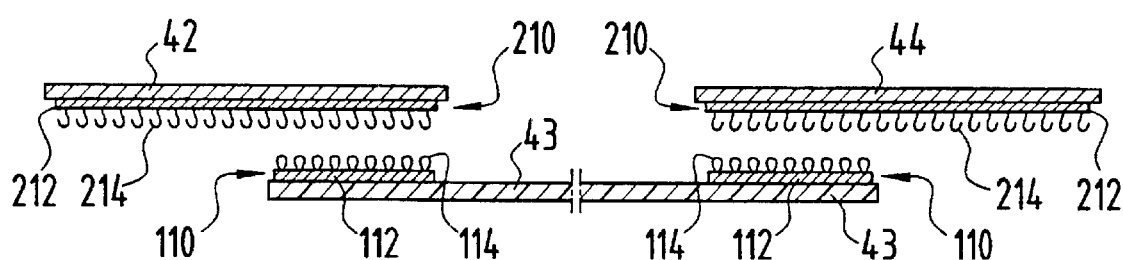
FIG. 2 shows a side view of a preferred embodiment of the fastening device of the present invention.

In FIG. 2, a preferred embodiment of the fastening device 40 of the present invention is shown. The first end member 42 and the second end member 44 comprise a first releasably engageable member 210. The suspension means 43 comprises at least one second releasably engageable member 110. The first releasably engageable member 210 is releasably engageable with the second releasably engageable member 110.

More preferably, the first releasably engageable members 210 and the second releasably engageable members 110 are components of a re-fastenable mechanical fastening means of the hook and loop type. The hook fastening material and receiving surface may be joined to the end members, the suspension members, the first end region or the second end region, respectively or the may be comprised in the end members, the suspension members, the first end region or the second end region, respectively.

The term "re-fastenable mechanical fastening system of the hook and loop type" as used herein refers to a multiply fastenable fastening system comprising a hook fastening material and a receiving surface.

The term "hook fastening material" as used herein refers to a material that comprises a substrate 212 and at least one prong 214 joined to the substrate. The term "substrate" as used herein refers to any exposed surface to which one or more prongs are joined. The term "prong" as used herein refers to. a means that is joined to a substrate, that extends outwardly from the surface of the substrate. Each prong comprises a base, a shank, and an engaging means. The base contacts and adheres to the substrate, and supports the proximal end of the shank. The shank projects outwardly from the substrate and the base and terminate in a distal end which is joined to an engaging means. The engaging means project laterally beyond the shanks in one or more directions and may resemble a hook shaped tine. The term "lateral" as used herein refers to a direction generally parallel to the surface of the substrate at the principal prong under consideration. The projection of an engaging means beyond the shank in a lateral direction allows the engaging means to be secured to a complementary receiving surface. The engaging means is joined to, and preferably contiguous with, the distal end of the shank.

The fastening system is secured to a complementary receiving surface. As used herein, the term "receiving surface" to which the engaging means of the fastening system are secured refers to any plane or surface having an exposed face with tightly spaced openings complementary to the engaging means and defined by one or more strands or fibers or, alternatively, which exposed face is capable of localized elastic deformation so that the engaging means may become entrapped and not withdrawn without interference or friction. The openings or localized elastic deformations allow for entry of the engaging means into the plane of the receiving surface, while the strands (or non-deformed material) of the receiving surface interposed between the openings (or deformed areas) prevent withdrawal or release of the fastening system until desired by the user or either the peel or shear strength of the fastening system is otherwise exceeded. The plane of the receiving surface may be flat or curved.

A receiving surface having strands or fibers, is said to be "complementary" if the openings between strands or fibers are sized to allow at least one engaging means to penetrate into the plane of the receiving surface, and the strands are sized to be engaged or intercepted by the engaging means. A receiving surface which is locally deformable is said to be "complementary" if at least one engaging means is able to cause a localized disturbance to the plane of the receiving surface, which disturbance resists removal or separation of the fastening system from the receiving surface.

Suitable receiving surfaces include reticulated foams, knitted fabrics, woven and nonwoven materials, and stitch-bonded loop materials, such as Velcro brand loop materials sold by Velcro USA of Manchester, N.H. A particularly suitable receiving surface is a polypropylene non-woven fabric having a basis weight of about 17.1 grams per square meter (0.5 ounces per square yard) made by any suitable commercial carding or spunbonding processes. Suitable non-woven fabrics can be obtained from Veratec Nonwoven Group of the International Paper Company of Walpole, Mass. 02081. Other receiving surfaces may also be used, such as stitchbonded fabric Number 970026 sold by the Milliken Company of Spartanburg, S.C.

In one embodiment of the present invention, the first releasably engageable members are hook fastening materials 210, preferably comprising hooks 214 and a substrate 212 (as is shown in FIG. 2). Accordingly, the second releasably engageable members are receiving surfaces, preferably comprising a backing 112 and a loop member 114. In another embodiment of the present invention, the first releasably engageable members are receiving surfaces and the second releasably engageable members are hook fastening materials.

In a preferred embodiment of the disposable absorbent article of the present invention, the first end member comprises a first releasably engageable member, the second end member comprises a first releasably engageable member, the first waist region comprises a second releasably engageable member, and the second waist region comprises a second releasably engageable member whereby said first releasably engageable members are releasably engageable with said second releasably engageable members. The second releasably engageable members are joined to the garment facing side of the backsheet or the backsheet comprises the second releasably engageable member, i.e. the backsheet or a region thereof may serve as a second releasably engageable member.

The releasable engagement between the end members of a fastening device and the first and second waist regions of the disposable absorbent article of the present invention can be achieved by hooks, buttons, press studs, adhesive tapes, mechanical fastening such as hook and loop type mechanical fastening, or the like.

In a preferred embodiment of the disposable absorbent article of the present invention, the first releasably engageable members comprised in the end members of the fastening devices and the second releasably engageable members comprised in the first and second waist regions are components of a mechanical fastening system of the hook and loop type. In one embodiment of the present invention, the first releasably engageable members are hook fastening materials. Accordingly, the second releasably engageable members are receiving surfaces. In another embodiment of the present invention, the first releasably engageable members are receiving surfaces and the second releasably engageable members are hook fastening materials.

In another preferred embodiment of the disposable absorbent article of the present invention, the suspension member is elastically extendible in the longitudinal direction. Preferably, the suspension member is elastically extendible to at least 120% of its contracted length, more preferably to at least 150% of its contracted length, most preferably to at least 200% of its contracted length.

The backsheet 26 is generally that portion of the diaper 20 positioned adjacent the garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 08/744,487, filed on Nov. 6, 1996 in the name of Curro. Other breathable backsheets including non-woven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. Preferably, one of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. No. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H. B. Fuller Company of St. Paul, Minnesota and marketed as HL-1258. Alternatively, the attachment means may comprise heat bonds, pressure bonds, ultrasonic bonds, dynamic mechanical bonds, or any other suitable attachment means or combinations of these attachment means as are known in the art.

In order to serve as a second releasably engageable member, the backsheet may be mechanically pre-treated according to PCT publication No. WO98/11855.

The topsheet 24 is preferably positioned adjacent the body surface 47 of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the absorbent assemblies include fibers, the fibers may be spunbond, carded, wetlaid, meltblown, hydroentangled, or otherwise processed as is known in the art. One suitable topsheet 24 comprising a web of staple length polypropylene fibers is manufactured by Veratec, Inc., a Division of International Paper Company, of Walpole, Massachusetts under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotioned Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysilozane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Johnson. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; and U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994. Each of these patents is incorporated herein by reference.

The diaper 20 may also comprise at least one elastic waist feature 34 that helps to provide improved fit and containment. The elastic waist feature 34 is generally intended to elastically expand and contract to dynamically fit the wearers waist. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

What is claimed is:

1. A disposable absorbent article having a first waist region and a second waist region, said disposable absorbent article comprising a topsheet, a backsheet at least partially peripherally joined to said topsheet, and an absorbent means positioned intermediate said topsheet and said backsheet, and a reusable fastening device comprising a first end member, a second end member, and a suspension member characterized in that said first end member and said second end member each comprising a first releasably engageable member, which comprises a first substrate and one or more hook type prongs having a base, a shank, and an engaging means, wherein said base of said one or more hook type prongs being adhered to said first substrate of said first releasably engaging member, said first waist region and said second waist region each comprising a second releasably engageable member, which comprises a second substrate and one or more loop type prongs having a base, a shank, and an engaging means, wherein said base of said one or more loop type prongs being adhered to the second substrate of said second releasably engaging member, said first end member is releasably engageable with said first waist region and releasably engageable with said suspension member, said second end member is releasably engageable with said second waist region and releasably engageable with said suspension member.

2. A disposable absorbent article according to claim 1 wherein said suspension member comprises at least one second releasably engageable member, said first releasably engageable member being releasably engageable with said second releasably engageable member.

3. A disposable absorbent article according to claim 1 wherein said first releasably engageable members being releasably engageable with said second releasably engageable members.

4. A disposable absorbent article according to claim 3 wherein said backsheet comprises said second releasably engageable members.

5. A disposable absorbent article according to claim 1 wherein said suspension member is elastically extendible in the longitudinal direction.

* * * * *

UNITED STATES PATENT AND TRADEMARK OFFICE
CERTIFICATE OF CORRECTION

PATENT NO.     : 6,520,947 B1
DATED          : February 18, 2003
INVENTOR(S)    : Tilly et al.

It is certified that error appears in the above-identified patent and that said Letters Patent is hereby corrected as shown below:

<u>Title page,</u>
Item [57], ABSRTACT,
Line 4, after first "end", insert -- member, --

<u>Column 3,</u>
Line 9, delete "Waist" and insert -- waist --.

<u>Column 5,</u>
Line 52, after "to", delete ".".

<u>Column 7,</u>
Line 53, delete "non-woven" and insert -- nonwoven --.

<u>Column 10, line 67 through Column 11, line 1,</u>
Delete "wearers" and insert -- wearer's --.

Signed and Sealed this

Eighth Day of June, 2004

JON W. DUDAS
*Acting Director of the United States Patent and Trademark Office*